US007670811B2

(12) United States Patent
Vercauteren et al.

(10) Patent No.: US 7,670,811 B2
(45) Date of Patent: Mar. 2, 2010

(54) PROCESS FOR PREPARING ISOMALTO-OLIGOSACCHARIDES WITH ELONGATED CHAIN AND LOW GLYCEMIC INDEX

(75) Inventors: Ronny Leontina Marcel Vercauteren, Beveren (BE); Van Sau Nguyen, Brussels (BE)

(73) Assignee: Cerestar Holding B.V., LA Sas van Gent (NL)

( * ) Notice: Subject to any disclaimer, the term of this patent is extended or adjusted under 35 U.S.C. 154(b) by 130 days.

(21) Appl. No.: 10/544,531

(22) PCT Filed: Feb. 5, 2004

(86) PCT No.: PCT/EP2004/001060
§ 371 (c)(1),
(2), (4) Date: Aug. 4, 2005

(87) PCT Pub. No.: WO2004/068966
PCT Pub. Date: Aug. 19, 2004

(65) Prior Publication Data
US 2006/0148040 A1 Jul. 6, 2006

(30) Foreign Application Priority Data
Feb. 8, 2003 (GB) ................. 0302894.1

(51) Int. Cl.
*C12P 19/04* (2006.01)
*C12P 19/00* (2006.01)
*C12P 19/18* (2006.01)
*C12N 9/10* (2006.01)

(52) U.S. Cl. ............ 435/101; 435/72; 435/97; 435/193

(58) Field of Classification Search ....... None
See application file for complete search history.

(56) References Cited

U.S. PATENT DOCUMENTS

| 4,649,058 A | * | 3/1987 | Schwengers | 426/658 |
| 4,673,643 A | * | 6/1987 | Schwengers | 435/97 |
| 6,025,168 A | * | 2/2000 | Vercauteren et al. | 435/97 |
| 7,435,564 B2 | * | 10/2008 | Serna-Saldivar et al. | 435/105 |

FOREIGN PATENT DOCUMENTS

EP  0 875 585 A1  11/1998
EP  875585 A1 * 11/1998

OTHER PUBLICATIONS

Tanriseven, A. and Dogan, S. Process Biochemistry. 2002, 37, 1111-1115.*
Albenne (Albenne, C, et al. "Molecular Basis of the Amylose-like Polymer Formation Catalyzed by *Neisseria polysaccharea* Amylosucrase" Journal of Biological Chemistry. 2004, 279(1), pp. 726-734. (available online: Oct. 21, 2003)).*
Monsan (Monsan, Pierre, et al. "Homopolysaccharides from Lactic Acid Bacteria" International Dairy Journal. 2001, 11, 675-685.).*
Remaud-Simeon (Remaud-Simeon, M., et al. "Glucansucrases: Molecular Engineering and Oligosaccharide Synthesis" Journal of Molecular Catalysis B: Enzymatic. 2000, 10, 117-128.).*
Robyt et al., "Relative, Quantitative Effects of Acceptors in the Reaction of *Leuconostoc mesenteroides* B-512F Dextransucrase", Carbohydrate Research, 121 (1983) pp. 279-286 (XP-001149187).
Sims et al., "Characterisation of Polysaccharides Synthesised by *Gluconobacter oxydans* NCIMB 4943", Carbohydrate Polymers 45 (2001) pp. 285-292.
Crittenden et al., "Production, Properties and Applications of Food-Grade Oligosaccharides", Trends in Food Science & Technology, Nov. 1996, vol. 7 pp. 353-361 (XP-002245493).

* cited by examiner

*Primary Examiner*—Christopher R Tate
*Assistant Examiner*—Aaron J Kosar
(74) *Attorney, Agent, or Firm*—Fitch, Even, Tabin & Flannery

(57) ABSTRACT

The invention relates to a process for preparing isomalto-oligosaccharides with elongated chain length. Isomalto-oligosaccharides are directly converted to isomalto-oligosaccharides with elongated chain length in the presence of glucansucrase. Said products can be applied in food, feed, beverages, cosmetics or pharmaceutical products and are particularly useful as slow or non-digestible oligosaccharides, low calorie providers, prebiotics, mineral absorption promoting agents, non-cariogenic agents and/or low glycemic index regulating syrups.

17 Claims, No Drawings

PROCESS FOR PREPARING ISOMALTO-OLIGOSACCHARIDES WITH ELONGATED CHAIN AND LOW GLYCEMIC INDEX

This Application is the National Phase of International Application No. PCT/EP04/001060 filed Feb. 5, 2004, which designated the U.S. and was published under PCT Article 21(2) in English, and this application claims, via the aforesaid International Application, the foreign priority benefit of and claims the priority from United Kingdom Application No. GB 0302894.1, filed Feb. 8, 2003, the complete disclosures of which are incorporated herein by reference.

TECHNICAL FIELD

The present invention relates to a process for preparing isomalto-oligosaccharides with elongated chain length and low glycemic index.

BACKGROUND OF THE INVENTION

Isomalto-oligosaccharides such as isomaltotriose and isomaltotetraose are known as growth-promoting saccharides for bifid bacteria and they will stimulate, in the large intestine, the growth of bacteria that are supposed to be beneficial for the health of the individual. The genus *Bifidobacteria*, in particular, is known to have a positive influence on the general health condition.

It is further described that the bifidus stimulating effect (i.e. the increase in bifidus population per weight unit of isomalto-oligosaccharide taken orally) is increased when going from a syrup rich in isomaltose (a disaccharide) towards isomaltotriose- and isomaltotetraose-containing syrups.

Consequently the most potent bifidus stimulating isomalto-oligosaccharide syrups will comprise of a high content of longer chain branched oligosaccharides like isomaltotriose, isomaltotetraose, isomaltopentaose, isomaltohexaose and higher analogues.

U.S. Pat. No. 4,649,058 relates to a process for preparing a gluco-oligosaccharide with elongated chains by reacting mono- or disaccharides as acceptors with sucrose in the presence of α-glucosyl transferase.

So far, the existing processes always start from a pure acceptor with low molecular weight, said acceptors being at most disaccharides.

There is therefore a need for a process which allows the use of mixtures wherein the acceptor is not limited by its molecular weight. The current inventor provides such a process.

SUMMARY OF THE INVENTION

The current invention relates to a process for elongating the chain length of isomalto-oligosaccharides characterised in that said process comprises an enzymatic transfer reaction between sucrose and isomalto-oligosaccharides present in a carbohydrate syrup. The enzymatic transfer reaction takes place in the presence of glucansucrase, wherein the glucansucrase is preferably selected from the group consisting of dextransucrase, alternansucrase, mutansucrase and mixtures thereof.

The invention further relates to a process comprising the following steps:
a) Using one or more isomalto-oligosaccharide producing enzymes to convert a malto-oligosaccharide syrup into a carbohydrate syrup containing isomalto-oligosaccharides,
b) Adding sucrose to the carbohydrate syrup containing isomalto-oligosaccharides,
c) Adding glucansucrase,
d) Converting the isomalto-oligosaccharides in the carbohydrate syrup into isomalto-oligosaccharides with elongated chain length for obtaining a syrupy mixture.

In particular, the invention relates to a process wherein the isomalto-oligosaccharide producing enzyme is transglucosidase.

Preferably, the current invention relates to a process wherein, between step a) and b), the carbohydrate syrup containing isomalto-oligosaccharides is purified by chromatography in order to remove glucose therefrom.

The current invention further relates to a process comprising chromatographic purification of a syrupy mixture containing isomalto-oligosaccharides with elongated chain length.

In a specific embodiment, the process step in the presence of one or more isomalto-oligosaccharide producing enzymes and/or the process step in the presence of glucansucrase is (or are) performed on a re-usable carrier.

Furthermore, the current invention relates to a syrup containing isomalto-oligosaccharides with elongated chain length which is obtainable by the previously described process.

Additionally, the current invention relates to the use of the syrup containing isomalto-oligosaccharides with elongated chain length in food, beverages, feed, cosmetics or pharmaceutical products.

It can be used as a slowly or non-digestible oligosaccharides, a low calorie provider, a prebiotic, a mineral absorption promoting agent, a non-cariogenic agent and/or a low glycemic index regulating syrup.

DETAILED DESCRIPTION

The current invention relates to a process for elongating chain length of isomalto-oligosaccharides characterised in that it comprises an enzymatic transfer reaction between sucrose and isomalto-oligosaccharides present in a carbohydrate syrup. The term "isomalto-oligosaccharide" as used herein refers isomalto-oligosaccharides comprising three or more monosaccharide units. The transfer reaction directly on isomalto-oligosaccharides immediately results in isomalto-oligosaccharides with elongated chain length.

The enzymatic transfer reaction takes place in the presence of glucansucrase. The glucansucrase is preferably selected from the group consisting of dextransucrase, alternansucrase, mutansucrase and mixtures thereof. By applying alternansucrase or mutansucrase, oligosaccharides with different linkages can be obtained.

The current invention further relates to a process comprising the following steps:
a) Using one or more isomalto-oligosaccharide producing enzymes for converting a malto-oligosaccharide syrup into a carbohydrate syrup containing isomalto-oligosaccharides,
b) Adding sucrose to the carbohydrate syrup;
c) Adding glucansucrase,
d) Producing a syrupy mixture by converting the isomalto-oligosaccharides in the carbohydrate syrup into isomalto-oligosaccharides with elongated chain length.

The isomalto-oligosaccharide producing enzyme can be selected from *Aspergillus* sp. strains (e.g. niger, oryzae, foetidus, carbonarius and arvamori), *Aureobasidium* sp. strains (e.g. Pullulans), *Moniella* sp. strains, *Brettanomyces* sp. strains, *Debaryomyces* sp. strains, *Aspergillus* sp. strains,

*Rhizopus* sp. strains, *Saccharomyces* sp. strains, *Leuconostoc* sp. and *Streptococcus* sp. In fact, any glucosyltransferase or α-glucosidase which allows the conversion of malto-oligosaccharides into isomalto-oligosaccharides can be used.

In particular, the present invention relates to a process wherein the isomalto-oligosaccharide producing enzyme is transglucosidase, whereby step a) is comparable to the enzymatic reaction described in EP 0 875 585.

The procedure consists, in a first step, of producing isomalto-oligosaccharides with a transglucosidase which acts on malto-oligosaccharide syrups (i.e. syrups containing maltose and/or maltotriose). During the synthesis of isomalto-oligosaccharides from maltose syrups in the presence of transglucosidase, a considerable amount (15-40% on total carbohydrate weight) of glucose is produced. When the desired composition of isomalto-oligosaccharides is obtained, sucrose and dextransucrase are added to the carbohydrate syrup to produce longer isomalto-oligosaccharide molecules (starting from the isomalto-oligosaccharides present in the carbohydrate syrup).

Since sucrose is no substrate for the transglucosidase, only dextransucrase will utilise the sucrose to elongate the isomalto-oligosaccharides.

In order to purify the isomalto-oligosaccharides and remove the considerable amounts of glucose formed during the transfer reaction, a chromatography can be applied between step a) and b) of current process.

The current invention further relates to a process comprising chromatographic purification of the syrupy mixture containing isomalto-oligosaccharides with elongated chain length.

In a specific embodiment, the process step in the presence of one or more isomalto-oligosaccharide producing enzymes and/or the process step in the presence of glucansucrase is performed on a re-usable carrier. In fact, the industrial viability is further improved by applying the one or more isomalto-oligosaccharide producing enzymes and/or the glucansucrase in immobilised form. The enzymes may be available in immobilised form such as cross-linked enzyme crystals. The enzymes can be immobilised on a carrier, more preferably immobilised on a re-usable carrier.

For the present purpose re-usable means that the carrier can be freed of enzyme or enzymatic activity in such a way that the carrier material stays intact. The carrier may be either continuously or intermittently refreshed. The carrier material can be re-loaded with enzyme and re-used. The cleaning of the carrier can, for example, be performed by washing with acidic or basic solution. This may be done in batch or in the column. It may be advantageous to add a salt Another possibility is the use of protein degrading enzymes. Yet another means would be heating of the material.

Preferably, the carrier is inert in the sense that it should not affect the conversion of the substrate into conversion product. Furthermore, the carrier is preferably described as being porous and substantially non-compressible. The term 'porous' is intended to mean that the solid carrier comprises a multitude of hollows and pores providing a large surface area. An example of the use of a porous material is the magnetically stabilised fluidised bed enzyme reactor. The term 'substantially non-compressible' is intended to mean that the solid carrier does not deform to any appreciable extent at the pressure which might prevail during the conversion process.

Preferably, materials are used which have anion exchange groups. Such materials may be on the basis of cellulose. Other more preferred carriers are polyacrylate or polystyrene based carriers having weakly basic groups. Weakly basic anion exchangers are materials having primary and/or secondary or/tertiary amino groups. They dissociate and have exchange capability in acidic solutions. The materials having tertiary amino groups have rather basic properties and they are also called medium basic anion exchangers. Preferably, phenol-formaldehyde based carriers are used, such as commercial available Duolite™ A 568 (Rohm and Haas).

Preferably, the carrier is an anion exchange resin and the enzyme is immobilized onto it by adsorption i.e. in a non-covalent manner. This enables the easy removal of the inactive enzyme and the subsequent reloading with fresh enzyme. Reloading of the carrier results in complete recovery of the activity of the conjugate. This means that the carrier material can be used for a considerable period of time before it has to be replaced. Also, a treatment with a cross-linking agent, such as glutaric dialdehyde can be performed to stabilise the immobilised enzymes.

Furthermore, the current invention relates to a syrup containing isomalto-oligosaccharides with elongated chain length and obtainable by the previously described process.

Additionally, the current invention relates to the use of the syrup containing isomalto-oligosaccharides with elongated chain length in food, beverages, feed, cosmetics or pharmaceutical products.

It can be used as a slowly or non-digestible oligosaccharides, a low calorie provider, a prebiotic, a mineral absorption promoting agent, a non-cariogenic agent, and/or a low glycemic index regulating syrup.

The specified syrup containing isomalto-oligosaccharides with elongated chain length is defined as a carbohydrate material which provides, compared to maltose, a slower release and, therefore, a slower absorption into the body of glucose during transit through the small intestine.

Applications of said specified syrup are many fold, i.e. they can be used to deliver sufficient carbohydrates to diabetic patients without a significant raise of the serum glucose level. Also, the addition of the specified syrup to the diet of elderly people confronted with a reduced glucose tolerance could have a beneficial effect.

In the domain of sports nutrition, said specified syrup could have interesting applications. Said syrup could supply an athlete with a steady and constant carbohydrate supply during physical exercise. Advantageously, the syrup may therefore be used as a component in sports or energy beverages.

The present invention also provides the use of said syrup in food or drink composition (=beverages). Typically, the food composition may be a diabetic food, a baby food, a diet food, for instance for sedentary people or a specially formulated food for people having a reduced glucose tolerance, for instance the elderly.

The presence of said syrup in food and drink compositions provides, as mentioned earlier, a slower release, and therefore a slower absorption into the body, of glucose. This is correlated with a low glycemic index.

The current invention has the following advantages:
 isomalto-oligosaccharides with elongated chain length can be prepared by a simple process,
 it is not necessary to use a pure acceptor for the production of isomalto-oligosaccharides with elongated chain length,
 isomalto-oligosaccharides are directly reacted to obtain isomalto-oligosaccharides with elongated chain length,
 products obtainable by the current process show several health beneficial effects which are useful in food, beverages, feed, cosmetics and pharmaceutical products.

The current invention is illustrated by way of the following examples.

EXAMPLE 1

A syrup (IMO, Composition: 20.4% DP1, 26.0% DP2, 31.2% DP3, 11.7% DP4, 3.9% DP5, 1.6% DP6, 0.8% DP7, 0.5% DP8, 0.3% DP9, 0.2% DP10, 3.4% DP>10; obtainable according to method of EP 0 875 585) was concentrated to 33% w/w and a sucrose solution at 33% w/w was added at different ratio's, going from 80/20 till 50/50 (v/v). The pH of the solutions was adjusted to 5.2 using 0.1 N HCl. All solutions were warmed up for 20 minutes at 30° C. and 2 ml of a dextransucrase solution with an activity of 3.7 U/ml was added to 20 ml of the prepared isomalto-oligosaccharide/sucrose solutions.

The solution was incubated at 30° C. and samples were taken after 48 hr of incubation. The samples were diluted with 3 ml demineralised water and put in a boiling water bath for 10 min. The solutions were filtered using a 0.45 μm filter and analysed by HPLC. The results obtained are displayed in Table 1:

TABLE 1

Final Composition is expressed as % (HPLC-results)

| Final comp. | Ratio substrate | | | |
|---|---|---|---|---|
| | IMO/sucrose 80/20 | IMO/sucrose 30/70 | IMO/sucrose 40/60 | IMO/sucrose 50/50 |
| Glucose | 17.9 | 16.6 | 15.6 | 15.2 |
| Fructose | 7.3 | 11.4 | 8.1 | 6.2 |
| Sucrose | 0.0 | 0.3 | 1.2 | 2.1 |
| DP2 | 15.6 | 11.7 | 9.3 | 8.3 |
| DP3 | 22.7 | 17.8 | 13.7 | 9.9 |
| DP4 | 18.3 | 19.8 | 19.2 | 16.8 |
| DP5 | 9.2 | 12.8 | 15.2 | 16.5 |
| DP6 | 2.7 | 3.9 | 5.6 | 7.2 |
| DP7 | 1.2 | 1.3 | 1.8 | 2.7 |
| DP8 | 0.5 | 0.5 | 0.6 | 1.1 |
| DP9 | 0.3 | 0.3 | 0.3 | 0.4 |
| DP10 | 0.3 | 0.1 | 0.1 | 0.3 |
| DP > 10 | 4.0 | 4.0 | 3.9 | 4.4 |

While the substrate has a high concentration for DP2-DP3, after the reaction of 48 hours, a high concentration is observed in the DP4-DP5 range (=isomalto-oligosaccharides with elongated chain length).

EXAMPLE 2

The syrup (IMO, Composition: 20.4% DP1, 26.0% DP2, 31.2% DP3, 11.7% DP4, 3.9% DP5, 1.6% DP6, 0.8% DP7, 0.5% DP8, 0.3% DP9, 0.2% DP10, 3.4% DP>10 obtainable according to method of EP 0 875 585) was concentrated to 33% w/w and a sucrose solution of 33% w/w was added at different ratio's, going from 80/20 till 50/50 (v/v). The pH of the solutions was adjusted to 5.2 using 0.1 N HCl. All solutions were warmed up for 20 minutes at 30° C. and 2 ml of a alternansucrase solution (Leuconostoc mesenteroides NRRL B-1355) with an activity of 6.6 U/ml was added.

The solution was incubated at 30° C. and samples were taken after 48 hr of incubation. The samples were diluted with 3 ml demineralised water and put in a boiling water bath for 10 min. The solutions were filtered using a 0.45 μm filter and analysed by HPLC. The results obtained are displayed in Table 2:

TABLE 2

Final Composition is expressed as % (HPLC-results)

| Final comp. | Ratio substrate | | | |
|---|---|---|---|---|
| | IMO/sucrose 80/20 | IMO/sucrose 30/70 | IMO/sucrose 40/60 | IMO/sucrose 50/50 |
| Glucose | 19.7 | 17.4 | 15.3 | 8.8 |
| Fructose | 6.0 | 10.4 | 15.4 | 19.2 |
| Sucrose | 0.0 | 0.0 | 0.0 | 2.5 |
| DP2 | 14.5 | 10.0 | 7.3 | 4.2 |
| DP3 | 25.3 | 19.2 | 14.1 | 8.4 |
| DP4 | 19.3 | 21.7 | 21.3 | 16.8 |
| DP5 | 8.3 | 13.8 | 15.5 | 20.7 |
| DP6 | 2.4 | 4.4 | 5.9 | 10.6 |
| DP7 | 0.9 | 1.5 | 2.0 | 4.5 |
| DP8 | 0.5 | 0.6 | 0.7 | 1.7 |
| DP9 | 0.2 | 0.2 | 0.2 | 0.5 |
| DP10 | 0.2 | 0.2 | 0.2 | 0.2 |
| DP > 10 | 2.6 | 2.9 | 2.0 | 1.9 |

While the substrate has a high concentration for DP2-DP3, after the reaction of 48 hours, a high concentration is observed in the DP4-DP6 range (=isomalto-oligosaccharides with elongated chain length).

In-Vitro Digestion of Syrup Prepared in Example 2

The IMO syrup (Composition: 20.4% DP1, 26.0% DP2, 31.2% DP3, 11.7% DP4, 3.9% DP5, 1.6% DP6, 0.8% DP7, 0.5% DP8, 0.3% DP9, 0.2% DP10, 3.4% DP>10; obtainable according to method of EP 0 875 585) and the syrup obtained in example 2 by the action of dextransucrase on a 50/50 IMO sucrose (v/v) solution, was incubated with porcine intestinal acetone powder at 37° C. and pH6 for 2 hours.

Maltose was taken as reference. The results are displayed in Table 3:

TABLE 3

| Syrup | % dextrose released compared to reference |
|---|---|
| Maltose | 100 |
| IMO | 26 |
| Elongated IMO (example 2) | 15.5 |

The results clearly demonstrate the slow digestibility of the syrup obtainable by the current invention.

The invention claimed is:

1. A process of elongating the chain length of isomalto-oligosaccharides, wherein said process comprises:
    (a) enzymatically converting a malto-oligosaccharide syrup with one or more isomalto-oligosaccharide-producing enzymes into a carbohydrate syrup containing isomalto-oligosaccharides;
    (b) preparing a solution containing the isomalto-oligosaccharides by adding sucrose to the carbohydrate syrup from (a), wherein the ratio by volume (v/v) of isomalto-oligosaccharides in the carbohydrate syrup from (a) to sucrose in said solution is in the range of from about 50:50 (v/v) to about 30:70 (v/v);
    (c) adding at least one glucansucrase to said carbohydrate syrup or to said solution in (b); and
    (d) in the presence of said glucansucrase, reacting the sucrose with the isomalto-oligosaccharides in the solution, thereby producing a syrupy mixture wherein said syrupy mixture contains isomalto-oligosaccharides having an elongated chain length.

2. The process of claim 1, wherein in step (a) the isomalto-oligosaccharide producing enzyme is transglucosidase.

3. The process of claim 1, wherein the process further comprises, between steps (a) and (b) removing glucose from the carbohydrate syrup by chromatographic purification.

4. The process of claim 1, wherein the process further comprises chromatographically purifying the syrupy mixture of step (d).

5. The process of claim 1, wherein the enzymatically converting with one or more isomalto-oligosaccharide-producing enzymes of step (a), the adding at least one glucansucrase of step (c), and/or the reacting in the presence of glucansucrase of step (d) is performed on a re-usable carrier.

6. The process of claim 1, wherein said at least one glucansucrase is selected from the group consisting of dextransucrase, alternansucrase, mutansucrase, and mixtures thereof.

7. The process of claim 1, wherein the at least one glucansucrase is dextransucrase.

8. The process of claim 1, wherein the at least one glucansucrase is alternansucrase.

9. The process of claim 1, wherein the at least one glucansucrase is mutansucrase.

10. A process for elongating the chain length of isomalto-oligosaccharides, the process comprising:

(a) mixing sucrose and a carbohydrate syrup to form a solution, said carbohydrate syrup containing isomalto-oligosaccharides;

(b) adding an enzyme to the solution, to enzymatically catalyze a transfer reaction between said sucrose and said isomalto-oligosaccharides, wherein the v/v ratio of said sucrose to said isomalto-oligosaccharides is 5000 (v/v) or more and wherein the enzyme comprises at least one glucansucrase, thereby producing a syrupy mixture containing isomalto-oligosaccharides having an elongated chain length.

11. The process of claim 10, wherein in said process the sucrose content of the solution is 60% (v/v).

12. The process of claim 10, wherein in said process the sucrose content of the solution is 70% (v/v).

13. The process of claim 10, wherein said enzyme is in an immobilized enzyme.

14. The process of claim 10, wherein in step (a) said mixing sucrose comprises mixing a 33% (w/w) solution of sucrose.

15. The process of claim 1, wherein in step (c) said at least one glucansucrase is added to said carbohydrate syrup.

16. The process of claim 1, wherein in step (b) the sucrose is a sucrose solution, and said sucrose solution is admixed with the carbohydrate syrup.

17. The process of claim 1, wherein in step (b), the adding of the sucrose to the carbohydrate syrup comprises adding a solution of the sucrose to the carbohydrate syrup, wherein the percent by weight (% (w/w)) sucrose in the sucrose solution is equal to the % (w/w) isomalto-oligosaccharide in the carbohydrate syrup.

* * * * *